United States Patent [19]
Audia et al.

[11] Patent Number: 5,356,935
[45] Date of Patent: Oct. 18, 1994

[54] REDUCED PHENANTHRENES

[75] Inventors: James E. Audia, Indianapolis; Thomas C. Britton, Carmel; Patrick G. Spinazze, Indianapolis, all of Ind.

[73] Assignee: Eli Lilly and Company, Indianapolis, Ind.

[21] Appl. No.: 166,471

[22] Filed: Dec. 13, 1993

[51] Int. Cl.$^5$ ............... A61K 31/335; A61K 31/135; C07C 211/42; C07D 303/32
[52] U.S. Cl. ............... 514/656; 514/183; 514/475; 514/510; 514/567; 514/619; 514/864; 514/880; 549/544; 552/1; 560/45; 562/452; 564/163; 564/427
[58] Field of Search ............... 514/183, 475, 656, 864, 514/880; 549/544; 552/1; 564/427

[56] References Cited

U.S. PATENT DOCUMENTS 2,889,341  6/1959  Hoehn ............... 260/348

FOREIGN PATENT DOCUMENTS 0469547  7/1991  European Pat. Off. ...... C07J 41/00
0469548  7/1991  European Pat. Off. ...... C07J 41/00

*Primary Examiner*—Peter O'Sullivan
*Attorney, Agent, or Firm*—Joseph A. Jones

[57] ABSTRACT

A series of dihydrophenanthreneones and tetrahydrophenanthreneones are useful as inhibitors of 5α-reductase, and a series of hexahydrophenanthreneones are useful as intermediates for preparing such pharmaceuticals.

16 Claims, No Drawings

REDUCED PHENANTHRENES

FIELD OF THE INVENTION

The present invention belongs to the fields of pharmaceutical chemistry and pharmacology, and provides reduced phenanthrenes which are pharmaceuticals for the inhibition of 5α-reductase.

BACKGROUND OF THE INVENTION

It is now widely known that certain undesirable physiological conditions such as benign prostatic hyperplasia, male pattern baldness, acne vulgaris, seborrhea, androgenic alopecia, hirsutis and prostate cancer are androgen mediated conditions dependent on dihydrotestosterone (DHT). The enzyme 5α-reductase mediates the conversion of testosterone to the more potent androgen DHT in various target organs. it has been demonstrated that inhibitors of 5α-reductase (SAR) should block the formation of DHT and ameliorate the above undesirable physiological conditions. At least one 5AR inhibitor, finasteride, is now in the marketplace and is approved for the treatment of benign prostatic hyperplasia. Mocellini, et al., *The Prostate* 22, 291–299 (1993).

Recently, it has been found that there are at least two 5AR isozymes in humans, Anderson, et al., *Proc. Natl. Acad. Sci. USA* 87, 3640–44 (1990); Andersson, et al., *Nature* 354, 159–61 (1991). The two isozymes exhibit some differences in their biochemical properties, genetics and pharmacology. The two 5AR isozymes (usually called type 1 and type 2) are now the subject of considerable research, which has not yet shown clearly the roles which each isozyme plays in the body.

The present invention provides a series of new compounds which are effective inhibitors of the 5AR isozymes.

SUMMARY OF THE INVENTION

The present invention provides compounds of the formula

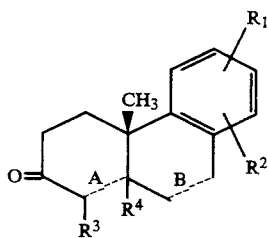

wherein each of dotted lines A and B represents a single bond or a double bond, provided that B does not represent a double bond unless A also represents a double bond;

$R^1$ and $R^2$ independently represent hydrogen, halo, trifluoromethyl, $C_1$–$C_4$ alkyl, —$(CH_2)_nCOR^5$ or

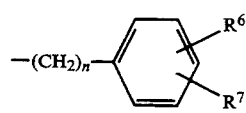

provided that no more than one of $R^1$ and $R^2$ represents hydrogen;

n represents 0–3;

$R^5$ represents hydroxy, $C_1$–$C_3$ alkyl, $C_1$–$C_3$ alkoxy, phenoxy, phenyl, amino, $C_1$–$C_3$ alkylamino or di($C_1$–$C_3$ alkyl)amino;

$R^6$ and $R^7$ independently represent hydrogen, $C_1$–$C_4$ alkyl, halo or trifluoromethyl;

when A is a single bond, $R^3$ and $R^4$ together represent epoxy;

when A is a double bond, $R^3$ represents amino or azido, and $R^4$ is absent.

The invention also provides a method of inhibiting 5AR in a patient in need of such treatment, comprising the administration of an effective 5AR-inhibiting amount of a compound of formula I wherein $R^3$ represents amino to such patient.

The invention further provides pharmaceutical compositions of the compounds of formula I, comprising pharmaceutically acceptable inert ingredients, and still further provides methods of treating benign prostatic hyperplasia, male pattern baldness, acne vulgaris, seborrhea, androgenic alopecia, hirsutism and prostatic cancer, comprising the administration of a compound of formula I to a patient in need of such treatment.

DETAILED DESCRIPTION OF THE INVENTION

Throughout the present document, all temperatures will be described in degrees Celsius, and all expressions of concentration, percentage and proportion will be expressed in weight units, unless otherwise stated.

The Compounds

The compounds of formula I cab be described as reduced phenanthrenes, and will be so named throughout this document. The positions of the phenanthrene structure are numbered as follows.

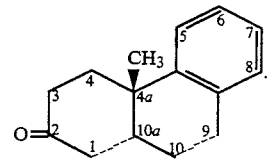

It will be understood that the phenanthrenes of formula I wherein both A and B represent double bonds are named as 4,4a-dihydro-2(3H)-phenanthreneones. Those where both A and B represent single bonds are named as 3,4,4a,9,10,10a-hexahydro-2(1H)-phenanthreneones, and those where line A represents a double bond are named as 4,4a,9,10-tetrahydro-2(3H)-phenanthreneones.

The reader will understand that many of the compounds of the present invention exist in more than one optically isomeric form. If no information is given about the optical form of a compound in this document, the racemic form and all optically isomeric forms are meant. When a specific optically isomeric form, or mixture of specific forms, is meant, the compound Will be specifically so named or described.

It will be noted that the methyl substituent at the 4a-position must be in the optical configuration indicated.

In the description of formula I, the various chemical terms carry their usual meanings. The term $C_1$–$C_4$ alkyl, in each appearance, refers to methyl, ethyl, propyl, isopropyl and the four isomeric butyl groups. The term $C_1$–$C_3$ alkyl refers to methyl, ethyl and the two isomeric propyl groups. The term halo refers to fluoro, chloro, bromo and iodo.

The dotted lines A and B in formula I indicate that the carbon atoms joined by those lines may be joined either by single or double bonds; however, the dotted line B may not represent a double bond unless there is also a double bond at the position of line A. The reader should note that the definitions of the groups $R^3$ and $R^4$ are affected by the saturated or unsaturated condition of line A.

The various alkoxy groups consist of the corresponding alkyl group linked through an oxygen atom to the underlying group.

The compounds of formula I wherein $R^3$ and $R^4$ combine to form epoxy, and those wherein $R^3$ is an azido group, are useful as intermediates for preparing those compounds wherein $R^3$ is amino, which are the 5AR inhibitors.

While all of the compounds of formula I are useful and valuable, whether as pharmaceuticals or as intermediates for preparing pharmaceuticals, certain groups of the compounds are preferred. One preferred group constitutes those compounds wherein $R^3$ is amino, and another is those where $R^3$ is amino or $R^3$ and $R^4$ combine to form epoxy.

Further preferred groups of compounds of formula I include that where A is a double bond; that where both A and B are double bonds; and that where $R^1$ represents hydrogen and $R^2$ represents halo or $C_1$-$C_4$ alkyl.

A further preferred group of compounds is that wherein $R^1$ and $R^2$ independently represent hydrogen, halo, trifluoromethyl or $C_1$-$C_4$ alkyl. Another preferred group is that wherein $R^1$ and $R^2$ independently represent hydrogen or —$(CH_2)_nCOR^5$, wherein $R^5$ is as defined above.

It will be understood that the various preferred groups can be combined to form additional, narrower preferred groups.

A group of exemplary substituents which can be represented by $R^1$ and $R^2$ will be specifically named, since those substitutents are indicated by general terms in formula I and the reader may need some additional exemplification and explanation.

hydrogen
chloro
bromo
trifluoromethyl
methyl
t-butyl
propyl
carboxy
2-carboxyethyl
acetyl
3-butyrylpropyl
methoxycarbonyl
2-(isopropoxycarbonyl)ethyl
phenoxycarbonyl
3-benzoylpropyl
aminocarbonyl
(methylamino)carbonylmethyl
3-(propylaminocarbonyl)propyl
dimethylaminocarbonyl
2-(ethylmethylaminocarbonyl)ethyl
phenyl
3,5-diethylphenyl
3-(4-isopropylphenyl)propyl
2-ethyl-4-fluorophenyl
3-t-butyl-5-trifluoromethylphenyl
4-iodo-2-propylphenyl
1-(3-iodo-4-acetylphenyl)ethyl
3-(4-butyl-3-isopropylphenyl)propyl
4-ethylphenyl
3-methyl-5-isobutylphenyl
2-bromo-5-propylphenyl
4-trifluoromethylphenyl
3-trifluoromethyl-4-chlorophenyl
3-isopropyl-4-trifluoromethylphenyl

Synthesis

The compounds of formula I are conveniently prepared from (S) -4,4a, 9,10-tetrahydro-4a-methyl-2 (3H) phenanthreneone, appropriately substituted to provide the $R^1$ and $R^2$ substituents. That intermediate is prepared according to Preparation 1, which follows.

The substituted 1-methyl-2-tetralones which are the ultimate starting materials are readily obtained in commerce or easily prepared by methods known to ordinarily skilled organic chemists.

The tetrahydrophenanthreneone intermediate is first converted to the 1,10a-epoxy intermediate, then to a 1-azido intermediate, and then to 1-amino pharmaceuticals according to the following scheme.

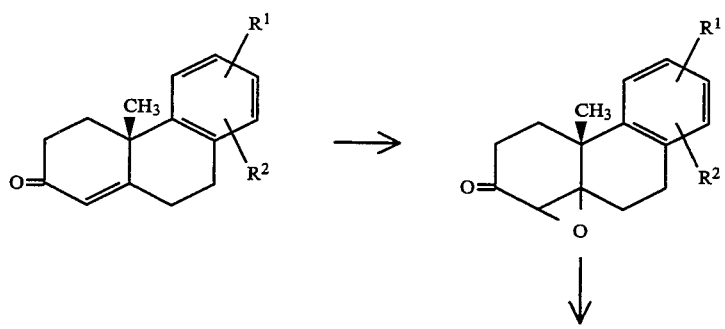

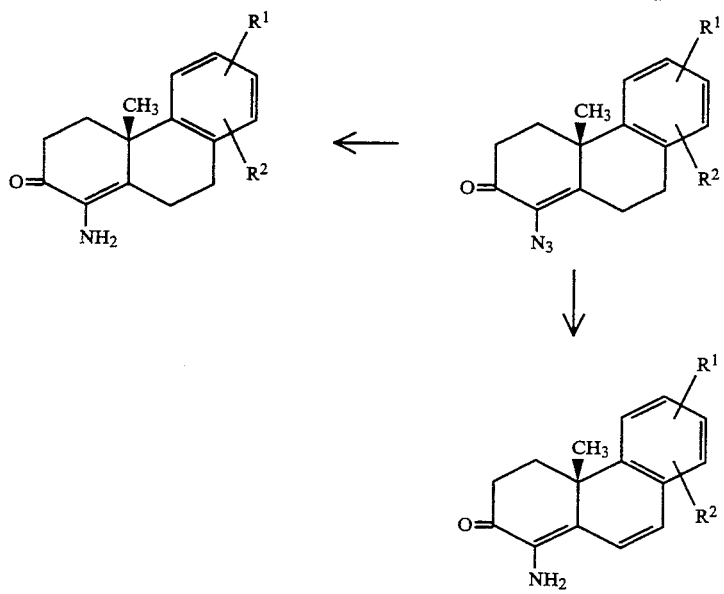

The epoxy intermediate is prepared by the reaction of the starting tetrahydrophenathreneone with a strong oxidizing agent, preferably hydrogen peroxide in strong aqueous base. Isolation in a neutral buffer produces the epoxy intermediate as a mixture of diastereomers, which are readily separated by chromatography. Preparation 2 below sets out the process in full.

The epoxy intermediate is converted to the 1-azide by reaction at moderately elevated temperature with an azide reagent such as trimethylsilyl azide. The azide is isolated, for example, as shown below in Preparation 3, and is converted to the 1-amino pharmaceuticals.

When a 1-amino tetrahydrophehanthreneone is desired, the azido intermediate is reacted with triphenylphosphine and water at an elevated temperature, such as the refluxing temperature of the reaction mixture in an inert solvent, most preferably tetrahydrofuran. On the other hand, if a 1-amino edihydrophenan-threneone, where dotted line B is a double bond, is to be made, the azido intermediate is reacted with a strong acid, preferably a mineral acid and most preferably sulfuric acid, at an elevated temperature, even as high as 100°, for a short period of time. Isolation by chromatography provides the desired dihydrophenanthreneone in economic yield.

The following preparations and examples further illustrate the synthesis of compounds of formula I.

PREPARATION 1

(S)-7-chloro-4,4a,9,10-tetrahydro-4a-methyl-2-(3H)-phenanthreneone

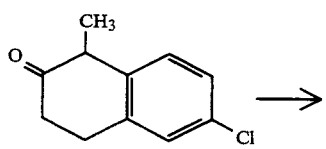

To a stirred solution of 6-chloro-1-methyl-2-tetralone (50.0 g, 0.256 mol.) in toluene (500 mL) was added (R)-(+)-1-phenethylamine (35 mL, 0.27 mol.). The solution was heated to reflux for 4 hours with azeotropic removal of water. The solution was allowed to cool to ambient temperature and was concentrated under reduced pressure to afford (R)-1-methyl-2-(1-methylbenzylamino)-6-chloro-3,4-dihydronaphthalene (79 g) as a yellow oil which was used without further purification.

To a stirred solution of the above intermediate (79 g, 0.25 mol.) in tetrahydrofuran (500 mL) was added methyl vinyl ketone (23 mL, 0.28 mol.) in a single portion. The solution was stirred under nitrogen in the dark for 96 hours. Aqueous acetic acid (20%, 500 mL) was added and the solution stirred for 2 hours. The reaction mixture was partitioned between ethyl acetate and water. The organic phase was washed with saturated sodium carbonate solution and dried over anhydrous sodium sulfate. The solution was concentrated under reduced pressure and the resultant oil was dissolved in anhydrous ethanol (100 mL) and added to a stirred solution of sodium ethoxide, prepared by careful addition of sodium (6.5 g) to anhydrous ethanol (500 mL). The solution was heated at 50° C. for 3 hours, cooled to ambient temperature, and partitioned between diethyl ether and water. The organic phase was washed with brine and dried over anhydrous sodium sulfate. Removal of solvent under reduced pressure and chromatography of the residue on silica (eluting with 25% ethyl acetate in hexanes) afforded the title compound (34 g) as a brown oil which solidified upon standing.

Optical rotation: +15.39° at 589 nm; MS m/e=246; melting range 94–96°.

Analysis Calculated for $C_{15}H_{15}ClO$. Theory: C, 73.02%; H, 6.13%; Found: C, 72.73%; H, 6.10%.

PREPARATION 2 cl (1aR, 4aS, 10aS)-7-chloro-1,10a-epoxy-4a-methyl3,4,4a, 9,10,10a-hexahydro-2 (1H) -phenanthreneone and (1aS, 4aS, 10aR) -7-chloro-1,10a-epoxy-4a-methyl-3,4,4a, 9,10,10a-hexahydro-2(1H ) -phenanthreneone

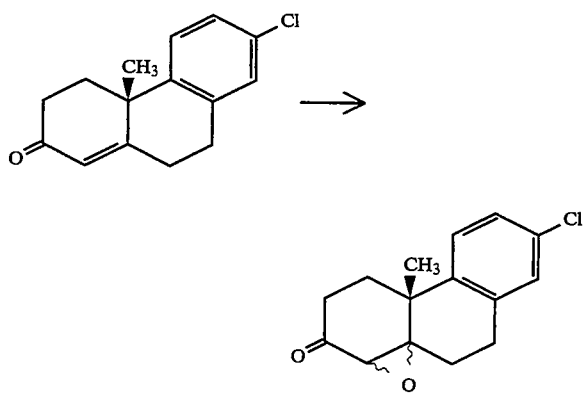

To a solution of (S)-7-chloro-4,4a,9,10-tetrahydro-4a-methyl-2(3H)-phenanthreneone (1.059g, 4.27 mmol) in methanol (18 mL) and methylene chloride (3.7 mL) at 0° was added 30% hydrogen peroxide (0.96 mL, 9.4 mmol) in one portion. The mixture was then lowly treated with a solution of aqueous sodium hydroxide (0.75 mL, 4.25 M, 3.20 mmol). After 1 hour at 0° and 4 hours at ambient the mixture was poured into pH 7 phosphate buffer (1M sodium dihydrogen phosphate, 1M disodium hydrogen phosphate) (200 mL) and extracted with 3 portions of dichloromethane (600 mL total). The combined organic extracts were dried over magnesium sulfate, filtered, evaporated and purified by flash chromatography on silica gel (1:4 ethyl acetate/hexane) to give 0.57 g (51%) of a white viscous oil which was a mixture of diastereomers. The mixture was separated by flash chromatography (1:9ethyl acetate/hexane) to give 0.377 g of the β-isomer as a white solid which eluted first and 0.182 g of the α-isomer as a white viscous oil which solidified with time.

β-Epoxide: IR (KBr) 1719 (CO)cm$^{-1}$; $^1$H NMR (300 MHz, CDCl$_3$) δ7.20 (s, 2H), 7.14 (s, 1H), 3.12 (s, 1H), 2.99–3.03 (m, 2H), 2.47–2.66 (m, 2H), 2.13 -2.23 (m, H) , 1.95–2.06 (m, 2H), 1.53 (s, 3H), 1.39–1.46 (m, 1H); MS (FD) m/z 262 (M+); UV $\lambda_{max}^{EtOH}$(nm) (ε) 203 (22758), 217 (9992).

Analysis Calculated for $C_{15}H_{15}ClO_2$: Theory: C, 68.57; H, 5.75; Found: C, 68.76; H, 5.87.

α-Epoxide: IR (KBr) 1711 (CO)cm$^{-1}$; $^1$H NMR (300 MHz CDCl$_3$) δ7.20 (s, 2H), 7.15 (s, 1H), 3.36 (s, 1H), 3.18 (m, 1H), 2.88 (ddd, J=16.7, 5.7, 1.5 Hz, 1H), 2.41–2.64 (m, 3H), 2.21–2.31 (m, 1H), 2.00 (ddd, J=13.3, 7.5, 1.4 Hz, 1H), 1.46 (ddd, J=14.5, 5.5, 1.5 Hz, 1H), 1.38 (s, 3H); MS (FD) m/z 262 (M+); UV $\lambda_{max}$-$^{EtOH}$(nm) (ε) 203 (25637), 216 (11105).

Analysis Calculated for $C_{15}H_{15}ClO_2$: Theory: C, 68.57; H, 5.75; Found: C, 68.70; H, 5.90.

PREPARATION 3

(R)-1-azido-7-chloro-4,4a,9,10-tetrahydro-4a-methyl-2(3H)-phenanthreneone

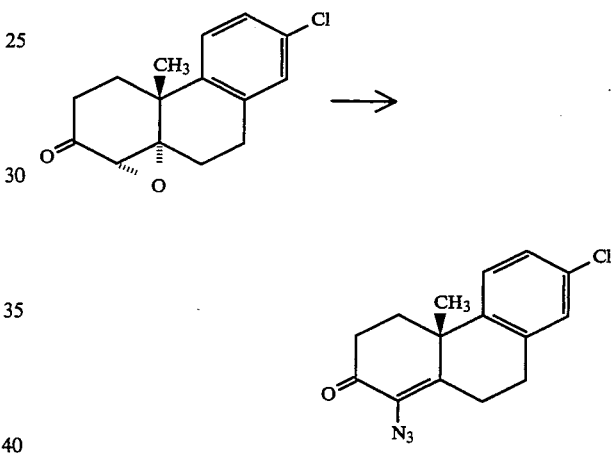

To a solution of (1aS, 4aS, 10aR)-7-chloro-1,10a-epoxy-4a-methyl-3,4,4a,9,10,10a-hexahydro-2(1H)phenanthreneone (1.105 g, 4.20 mmol) in dimethylformamide (25 mL) under nitrogen was added trimethylsilyl azide (1.12 mL, 8.41 mmol) and methanol (0.34 mL, 8.41 mmol). After stirring at 60° for 16 hours the mixture was diluted with diethyl ether (150 mL) and washed three times with brine (total 100 ml). The organic fraction was dried over magnesium sulfate, filtered, evaporated and purified by preparative high performance liquid chromatography on silica gel (gradient: hexane —>25% ethyl acetate/hexane) to give 0.247 g (20%) of the title compound as a light yellow powder. IR (KBr) 2107 (N$_3$), 1671 (CO)cm$^{-1}$; $^1$H NMR (300 MHz, CDCl$_3$) δ7.22 (s, 2H), 7.13 (s, 1H), 3.09–3.17 (m, 1H), 2.92–3.01 (m, 1H), 2.75–2.90 (m, 2H), 2.66 (ddd, J =17.9, 4.9, 2.4 Hz, 1H), 2.33 -2.44 (m, 2H), 2.07 (m, 1H), 1.55 (s, 3H); MS (FD) m/z 287 (M+);UV $\lambda_{max}$-$^{EtOH}$(nm) (ε) 204 (24710), 280 (11353).

Analysis Calculated for $C_{15}H_{14}C_1N_3O$: Theory: C, 62.61; H, 4.90; N, 14.60; Found; C, 62.80; H, 5.03; N, 14.37.

EXAMPLE 1

(R)-1-amino-7-chloro-4,4a,9,10-tetrahydro-4a-methyl-2(3H)-phenanthreneone

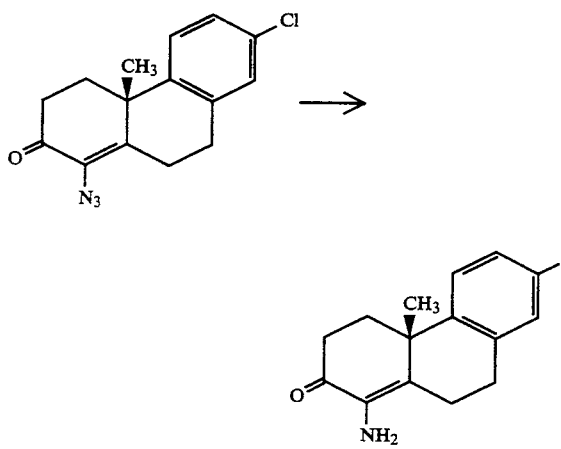

To a solution of (R) -1-azido-7-chloro-4,4a, 9,10-tetrahydro-4a-methyl-2 (3H) -phenanthreneone (0.210 g, 0.730 mmol) in tetrahydrofuran (8 mL) and water (1 mL) was added triphenylphosphine (0.325 g, 1.24 mmol). After refluxing for 20 minutes the mixture was cooled and the tetrahydrofuran evaporated. The resulting system was diluted with toluene (8 mL) and refluxed for 16 hours. The mixture was evaporated and the residue was purified by chromatography (Chromatotron, Harrison Research, Palo Alto, Calif.) (15% ethyl acetate/hexane) twice to give 42 mg (22%) of the title amine as a white powder. IR (KBr) 1648 (CO)cm$^{-1}$; $^1$H NMR (300 MHz, CDCl$_3$) δ7.23 (s, 2H), 7.15 (s, 1H), 2.98–3.07 (m, 1H), 2.75–2.93 (m, 3H), 2.48–2.67 (m, 2H), 2.36–2.47 (m, 1H), 2.05–2.16 (m, 1H), 1.49 (s,3H); MS (FD)m/z 261 (M+); UV $\lambda_{max}^{EtOH}$(nm) (ε) 203 (20595), 294 (6036).

Analysis Calculated for C$_{15}$H$_{16}$ClNO: Theory: C, 68.83; H, 6.16; N, 5.35; Found: C, 68.58; H, 6.25; N, 5.07.

EXAMPLE 2

(R)-1-amino-7-chloro-4,4a-dihydro-4a-methyl-2(3H)-phenanthreneone

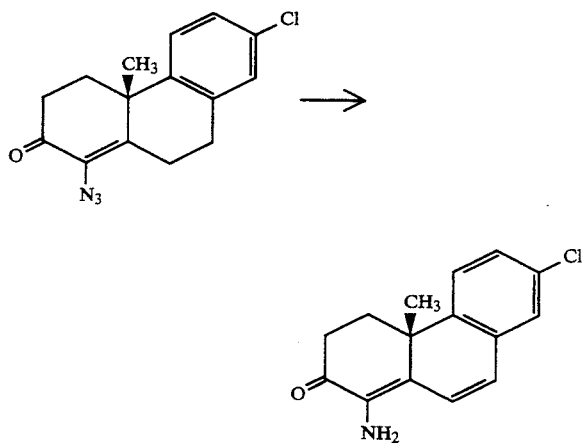

To a solution of (R)-1-azido-7-chloro-4,4a,9,10-tetrahydro-4a-methyl-2(3H)-phenanthreneone (0.227 g, 0.789 mmol) in dimethylsulfoxide (20 mL) was added sulfuric acid (50 μl, 0.947 mmol) and the mixture was warmed to 100°. After 90 minutes the mixture was cooled to 25°, diluted with ethyl acetate (200 mL) and washed with water (50 mL). The solution was dried over magnesium sulfate, filtered, evaporated and the residue was purified by radial chromatography (Chromatotron, Harrison Research, Palo Alto, Calif.) (20% ethyl acetate/hexane) to give 0.041 g (20%) of the title diene amine as a white foam. IR (KBr) 1666 (CO)cm$^{-1}$; $^1$H NMR (300 MHz, CDCl$_3$) δ 7.19–7.26 (m 2H), 7.16 (m, 1H), 6.56 (s, 2H), 3.97 (bs, 2H), 2.66–2.85 (m, 2H), 2.57 (ddd, J=12.9, 4.9, 2.6 Hz, 1H, 1H), 2.27 (m, 1H), 1.37 (s, 3H); MS (FD) m/z 259 (M+); UV $\lambda_{max}^{EtOH}$(nm) (ε)203 (23557), 264 (8392), 399 (12937).

Analysis Calculated for C$_{15}$H$_{14}$ClNO: Theory: C, 69.37; H, 5.43; N, 5.39; Found: C, 69.54; H, 5.44; N, 5.56.

Compounds of the present invention have been shown to be inhibitors of both Type I and Type II 5AR in tests carried out according to the following method, which is adapted to routine use.

Methodology of Human Type I and Type II Steroid 5α-Reductase Assays

Preparation of Type I 5α-Reductase from Human Scalp

Scalp punch biopsies from graft recipient sites were obtained from human hair transplant procedures immediately after surgery and were frozen on dry ice and stored at −80° C. Approximately 60–75 punches from one surgical procedure were used to generate an enzyme preparation. The subcutaneous tissue was cut away and discarded. The skin was frozen with liquid nitrogen and pulverized to powder. The powder was homogenized in 30 ml of ice-cold buffer (20 mM Tris-HCl, pH 7.5) using a Brinkmann Polytron (Westbury, N.Y.) with a PTA 10-S robe and a setting of 7. The homogenization procedure consisted of four 15 second pulses. Connective tissue was cleared from the probe with forceps between pulses. The homogenate was then filtered through cheese cloth and the filtrate centrifuged at 100,000×g for one hour in a Beckman L8-60M ultracentrifuge. The pellet was resuspended by homogenization with a Dounce homogenizer using the same buffer solution. An aliquot was taken for protein determination by the Lowry method, Lowry, et al., Protein Measurement with the Folin Phenol Reagent, J. Biol. Chem., 193,265–75 (1951). Aliquots of the enzyme preparation were stored at −80° until use.

Preparation of Type II 5α-Reductase from Human Prostate

The same procedure as above was used for preparations using tissue from prostate surgery with the following changes: The buffer used was 20 mM sodium phosphate, pH 6.5; and the pellet was resuspended in the sodium phosphate buffer containing 20% glycerol.

Human Scald 5α-Reductase Assay

This enzyme assay is based on the conversion of [$^3$H]-testosterone to [$^3$H]-5α-dihydrotestosterone (DHT) and other 5α-reduced metabolites. While about 90% of the 5α-reduced metabolites formed in these assays was DHT, androstanedione was formed at about 10%. Essentially no androsterone was detected. In a total volume of 1.0 ml, the assay contained 2.6 μCi [$^3$H]-testosterone (50 nM), 500 μM of reduced nicotine adeninc dinucleotide phosphate, 100 mM Tris-HCl, pH 7.5, (in Type II assays, 40 mM sodium acetate at pH 5.5 is used instead of Tris-HCl) and test compounds as indicated. Test compounds were added in 20 µl of dimethylsulfoxide (20 µl of dimethylsulfoxide was added to blanks and controls). The reaction was initiated by the addition of 0.5 mg of Type I or Type II 5α-reductase. The reaction mixture was incubated for 30 min at 25° and terminated by the addition of 1 ml ice-cold stopping solution. The stopping solution contained 40 µM each of non-radioactive testosterone, DHT, androstenedione, androstanedione, androsterone, androstan-3β,17β-diol, and androstan-3α,17β-diol.

The samples were prepared for high performance liquid chromatography by solid phase extraction. Disposable solid matrix extraction columns (C-18 reversed;phase, 6 ml, 500 mg; Bond Elut TM from Analytichem International; Harbor City, Calif.) were conditioned by washing with 5 ml of methanol followed by 5 ml of deionized water. The reaction mixtures were then applied to the columns. The columns were subsequently washed with 5 ml of acetone:water (1:4), followed by 0.3 ml of methanol. The samples were then eluted with 3 ml of methanol and collected in 20 ml scintillation vials. Three ml of water was then added to each scintillation vial. The solutions were then transferred to tubes and centrifuged for 30 min at 1000×g to remove any particulate material before chromatography.

The [$^3$H]-testosterone substrate and its metabolites were separated by chromatography using a C-18 reversed phase column (Beckman Ultrasphere 5 µm spherical 80A pore, part no. 235329, 4.6 mm i.d.×25 mm length) with an isocratic mobile phase (46 water: 46 methanol: 8 tetrahydrofuran by volume). The column temperature was maintained at 35° and the flow rate was 1.5 ml/min. A 400 µl aliquot was injected onto the column and radioactivity was determined using a Beckman 171 in-line flow radioisotope detector in conjunction with Rainin Dynamax TM software and a Macintosh computer. The flow rate of the Atomflow TM scintillation fluid was 4.5 ml / min.

The results of the assays on representative compounds are reported below as percent inhibition of Type I and Type II 5AR produced by each compound, compared to control reaction mixtures.

| Compound | Concentration | Type I | Type II |
| --- | --- | --- | --- |
| Example 1 | 10 µM | | 63% |
| | 3 | | 49 |
| | 1 | | 55 |
| | .3 | | 47 |
| | .1 | 42% | |
| | .03 | 35 | |
| | .01 | 0 | |
| Example 2 | 10 | | 36 |
| | 3 | | 33 |
| | 1 | | 16 |
| | .3 | | 7 |
| | .1 | 26 | |
| | .03 | 3 | |
| | .01 | 0 | |

As noted above, the compounds of the present invention are useful for inhibiting the conversion of testosterone to 5α-dihydrotestosterone. Therefore, another embodiment of the present invention is a method for inhibiting 5α-reductase by administering to a mammal in need of 5α-reductase inhibition a 5α-reductase inhibiting dose (effective amount) of a pharmaceutical compound according to Formula I.

The term "effective amount" as used herein means an amount of a compound of the present invention which is capable of inhibiting the conversion of testosterone to 5α-dihydrotestosterone which is catalyzed by the enzyme 5α-reductase and particularly, inhibiting 5α-reductase. The 5α-reductase inhibition contemplated by the present method includes both medical therapeutic and/or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.01 mg/kg to about 50 mg/kg of body weight of the active compound of this invention. Preferred daily doses generally will be from about 0.05 to about 20 mg/kg and most preferably from about 0.1 to about 10 mg/kg.

A variety of physiologic functions have been associated with 5α-dihydrotestosterone. The compounds of this invention are therefore believed to have the ability to treat in mammals a variety of disorders associated with 5α-dihydrotestosterone including benign prostatic hyperplasia (or hypertrophy), male pattern baldness, acne vulgaris, hirsutism and prostatic cancer. Therefore, the present invention also provides methods of treating the above disorders at the rates set forth above for inhibiting the 5α-reductase catalyzed conversion of testosterone to 5α-dihydrotestosterone.

The compounds can be administered by a variety of routes including oral, rectal, transdermal, subcutaneous, intravenous, intramuscular, intranasal, and topical for male pattern baldness, ache vulgaris, and hirsutism. The compounds of the present invention are preferably formulated prior to administration. Therefore, another embodiment of the present invention is a pharmaceutical formulation comprising am effective amount of a compound of Formula I and a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually admixed with a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders and the like. Typical formulations designed for topical administration are ointments, creams, gels, and lotions containing, for example, up to 10% by weight of the active compound.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example, anhydrous lanolin. Customarily, following formation of the base, whether oleaginous or absorbent, the active ingredient is added in an amount affording the desired concentration.

Creams are oil/water emulsions. They consists of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium ladryl sulfate; hydrophilic colloids, such as acacia, colloidal clays, veegum, and the like. Upon formation of the emulsion, the active ingredient customarily is added in an amount to achieve the desired concentration.

Gels comprise a base selected from an oleaginous base, water, or an emulsion-suspension base, such as described above. To the base is added a gelling agent which forms a matrix in the base, increasing its viscosity. Examples of gelling agents are hydroxypropylcellulose, acrylic acid polymers, and the like. Customarily, the active ingredient is added to the formulation at the desired concentration at a point preceding addition of the gelling agent.

The following formulation examples are illustrative only and are not intended to limit the scope of the invention in any way.

FORMULATION 1

Hard gelatin capsules are prepared using the following ingredients

| | Quantity (mg/capsule) |
|---|---|
| 1-Amino-6-bromo-8-ethyl-4,4a,9,10-tetrahydro-4a-methyl-2(3H)-phenanthreneone | 250 |
| Starch, dried | 200 |
| Magnesium stearate | 10 |
| Total | 460 mg |

FORMULATION 2

A tablet is prepared using the ingredients below:

| | Quantity (mg/capsule) |
|---|---|
| 1-Amino-8-acetyl-4,4a,9,10-tetrahydro-4a-methyl-2(3H)-phenanthreneone | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

| | Weight |
|---|---|
| 1-Amino-5-carboxyethyl-4,4a,9,10-tetrahydro-4a-methyl-2(3H)-phenanthreneone | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| | |
|---|---|
| 1-Amino-6,7-bis(trifluoromethyl)-4,4a-dihydro-4a-methyl-2(3H)-phenanthreneone | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

| | |
|---|---|
| 1-Amino-6-(2-[4-chlorophenyl]ethyl]-4,4a,dihydro-4a-methyl-2(3H)-phenanthreneone | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatine capsules in 200 mg quantities.

FORMULATION 6

Suppositories, each containing 225 mg of active ingredient, are made as follows:

| | |
|---|---|
| 1-Amino-5-(2-aminocarbonylethyl)-4,4a-dihydro-4a- | 225 mg |

| | |
|---|---|
| -continued | |
| methyl-2(3H)-phenanthreneone | |
| Saturated fatty acid glycerides | 2.000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| | |
|---|---|
| 1-Amino-8-phenoxycarbonyl-4,4a-dihydro-4a-methyl-2(1H)phenanthreneone | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the soidum carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---|
| 1-Amino-6-benzoylmethyl-4,4a,9,10-tetrahydro-4a-methyl-2(1H)-phenanthreneone | 100 mg |
| Isotonic saline | 1,000 ml |

The solution of the above ingredients generally is administered intravenously to a subject at a rate of 1 ml per minute.

The amount of active ingredient incorporated into the formulation of this invention is not critical; the concentration should only be in a range sufficient to permit ready administration of the formulation in an amount which will deliver the desired amount of active ingredient.

We claim:

1. A compound of the formula I

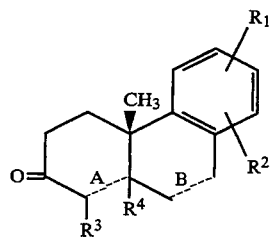

wherein each of dotted lines A and B represents a single bond or a double bond, provided that B does not represent a double bond unless A also represents a double bond;

$R^1$ and $R^2$ independently represent hydrogen, halo, trifluoromethyl, $C_1$-$C_4$ alkyl, —$(CH_2)_n COR^5$, or

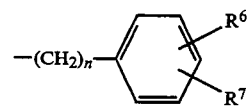

provided that no more than one of $R^1$ and $R^2$ represents hydrogen;

n represents 0–3;

$R^5$ represents hydroxy, $C_1$-$C_3$ alkyl, $C_1$-$C_3$ alkoxy, phenoxy, phenyl, amino, $C_1$-$C_3$ alkylamino or di ($<C_1$-$C_3$ alkyl) amino;

$R^6$ and $R^7$ independently represent hydrogen, $C_1$-$C_4$ alkyl, halo or trifluoromethyl;

when A is a single bond, $R^3$ and $R^4$ together represent epoxy;

when A is a double bond, $R^3$ represents amino or azido, and $R^4$ is absent.

2. A compound of claim 1 wherein each of dotted lines A and B represents a double bond.

3. A compound of claim 1 wherein line A represents a double bond and line B represents a single bond.

4. A compound of claim 2 wherein $R^3$ represents amino.

5. A compound of claim 3 wherein $R^3$ represents amino.

6. A compound of claim 1 wherein $R^3$ represents azido.

7. A compound of claim 1 wherein $R^3$ and $R^4$ combine to represent epoxy.

8. A compound of claim 1 wherein $R^1$ and $R^2$ independently represent hydrogen, halo, trifluoromethyl or $C_1$-$C_4$ alkyl.

9. A compound of claim 4 wherein $R^1$ and $R^2$ independently represent hydrogen, halo, trifluoromethyl or $C_1$-$C_4$ alkyl.

10. A compound of claim 5 wherein $R^1$ and $R^2$ independently represent hydrogen, halo, trifluoromethyl or $C_1$-$C_4$ alkyl.

11. The compound of claim 1 Which is (R)-1-amino-7-chloro-4,4a,9,10-tetrahydro-4a-methyl-2(3H)phenanthreneone.

12. The compound of claim 1 Which is (R)-1-amino-7-chloro-4,4a-dihydro-4a-methyl-2(3H)phenanthreneone.

13. A pharmaceutical composition comprising a pharmaceutically acceptable carrier and a compound of claim 4.

14. A pharmaceutical composition comprising a pharmaceutically acceptable carrier and a compound of claim 5.

15. A pharmaceutical composition comprising a pharmaceutically acceptable carrier and a compound of claim 8.

16. A pharmaceutical composition comprising a pharmaceutically acceptable carrier and a compound of claim 9.

* * * * *